US011161994B2

(12) United States Patent
Illsley et al.

(10) Patent No.: US 11,161,994 B2
(45) Date of Patent: Nov. 2, 2021

(54) ENERGY CURABLE COMPOSITIONS COMPRISING POLYOLS

(71) Applicant: SUN CHEMICAL CORPORATION, Parsippany, NJ (US)

(72) Inventors: Derek Ronald Illsley, Frome (GB); Shaun Lawrence Herlihy, Glastonbury (GB); Stephen Anthony Hall, Wells (GB); Jürgen Dieker, Karlstein am Main (DE)

(73) Assignee: Sun Chemical Corporation, Parsippany, NJ (US)

( * ) Notice: Subject to any disclaimer, the term of this patent is extended or adjusted under 35 U.S.C. 154(b) by 0 days.

(21) Appl. No.: 16/979,278

(22) PCT Filed: Jul. 1, 2019

(86) PCT No.: PCT/GB2019/051858
§ 371 (c)(1),
(2) Date: Sep. 9, 2020

(87) PCT Pub. No.: WO2020/012159
PCT Pub. Date: Jan. 16, 2020

(65) Prior Publication Data
US 2021/0054221 A1 Feb. 25, 2021

Related U.S. Application Data

(60) Provisional application No. 62/697,438, filed on Jul. 13, 2018, provisional application No. 62/716,472, (Continued)

(51) Int. Cl.
*C09D 11/101* (2014.01)
*A61L 2/08* (2006.01)
(Continued)

(52) U.S. Cl.
CPC ............ *C09D 11/101* (2013.01); *A61L 2/087* (2013.01); *B41M 1/04* (2013.01); *B41M 5/0047* (2013.01); *B41M 5/0064* (2013.01); *B41M 7/0081* (2013.01); *C09D 11/033* (2013.01); *C09D 11/037* (2013.01); *C09D 11/107* (2013.01); *C09D 11/322* (2013.01); *C09D 11/36* (2013.01);
(Continued)

(58) Field of Classification Search
CPC ... B41J 2/01; B41J 2/211; B41J 2/1433; B41J 2/17; B41J 2/17593; B41J 2/2107; B41J 2/1755; B41J 2/2114; B41J 2/2117; B41J 2/2056; B41J 2/21; B41J 2/0057; B41J 3/60; B41J 2002/012; B41J 2/04598; B41J 2/04588; B41J 2/04595; B41J 2/04586; B41J 2/14274; B41J 2/1623; B41J 2202/00; B41J 2202/03; B41J 2/14201; B41J 2/045; B41J 11/0015; B41J 11/002; B41J 2/04581; B41J 2/055; B41J 2/16538; B41J 2002/16502; B41J 29/02; B41J 2/17513; B41J 2/17509; B41J 29/13; B41J 2/17553; B41J 2/1606; B41J 2/1642; B41J 2/1609; B41J 2/164; B41J 2/162; B41J 2/161; B41J 2/19; B41J 15/04; B41J 25/001; B41J 25/34; B41J 25/003; B41J 25/312; B41J 2025/008; B41J 2202/21; B41J 2/17596; B41J 2/16508; B41J 2/1652; B41J 2/175; B41J 2/17563; C09D 11/36; C09D 11/40; C09D 11/30; C09D 11/38; C09D 11/32; C09D 11/322; C09D 11/324; C09D 11/328; C09D 11/101; C09D 11/102; C09D 11/005; C09D 11/54; C09D 11/52; C09D 11/106; C09D 11/326; C09D 11/107; C09D 11/03; C09D 11/037; C09D 1/033; B41M 5/0011; B41M 5/0017; B41M 5/0023; B41M 5/0047; B41M 7/00; B41M 7/0072; B41M 5/52; B41M 5/5218; B41M 5/5227
See application file for complete search history.

(56) References Cited

U.S. PATENT DOCUMENTS 6,846,851 B2    1/2005  Nakhmanovich
9,458,334 B1 *  10/2016 Samuel ................. C09D 11/38
(Continued)

FOREIGN PATENT DOCUMENTS

EP    2 508 575 A1    10/2012
EP    2 636 709 A1    9/2013
(Continued)

OTHER PUBLICATIONS

International Search Report issued in International Application No. PCT/GB2019/051858, dated Sep. 2, 2019.
(Continued)

*Primary Examiner* — Manish S Shah
(74) *Attorney, Agent, or Firm* — Marian E. Fundytus; Ostrolenk Faber LLP.

(57) ABSTRACT

Energy curable compositions including polyols, and any blend of ethylenically unsaturated monomers and oligomers. The polyols of the invention are essentially free of any ethylenically unsaturated groups. It is preferred that the polyol substances according to the invention have greater than one hydroxy group and preferably have boiling points in excess of 170° C. The compositions of the invention are particularly useful for the printing or coating of food packaging and may be applied via any printing or coating method, although inkjet printing is a preferred method.

19 Claims, No Drawings

Related U.S. Application Data filed on Aug. 9, 2018, provisional application No. 62/729,097, filed on Sep. 10, 2018, provisional application No. 62/760,142, filed on Nov. 13, 2018, provisional application No. 62/818,772, filed on Mar. 15, 2019.

(51) Int. Cl.
| | | |
|---|---|---|
| *B41M 5/00* | (2006.01) | |
| *B41M 7/00* | (2006.01) | |
| *C09D 11/033* | (2014.01) | |
| *C09D 11/037* | (2014.01) | |
| *C09D 11/107* | (2014.01) | |
| *C09D 11/322* | (2014.01) | |
| *C09D 11/36* | (2014.01) | |
| *B41M 1/04* | (2006.01) | |

(52) U.S. Cl.
CPC ....... *A61L 2202/18* (2013.01); *A61L 2202/23* (2013.01)

(56) References Cited

U.S. PATENT DOCUMENTS

| | | |
|---|---|---|
| 9,550,898 B2 | 1/2017 | Loccufier |
| 9,701,856 B2 | 7/2017 | Loccufier |
| 9,714,355 B2 | 7/2017 | Illsley |
| 9,796,865 B2 | 10/2017 | Claes |
| 2018/0030298 A1* | 2/2018 | Yamazaki ................ B41J 2/01 |

FOREIGN PATENT DOCUMENTS

| | | |
|---|---|---|
| JP | 2002 226757 A | 8/2002 |
| JP | 2004131587 A * | 4/2004 |
| WO | WO 2008/071994 A1 | 6/2008 |
| WO | WO2011/021052 A2 | 2/2011 |
| WO | WO2013/093414 A2 | 6/2013 |
| WO | WO2015/148094 | 10/2015 |
| WO | WO 2017/047615 A1 | 3/2017 |
| WO | WO2017/151137 | 9/2017 |
| WO | WO2017/180491 | 10/2017 |
| WO | WO2017/180496 | 10/2017 |
| WO | WO 2018/022590 A1 | 2/2018 |

OTHER PUBLICATIONS

Written Opinion of the International Searching Authority issued in International Application No. PCT/GB2019/051858, dated Sep. 2, 2019.

International Preliminary Report on Patentability (Chapter II of the Patent Cooperation Treaty) issued in International Application No. PCT/GB2019/051858, dated Jul. 8, 2020.

* cited by examiner

ENERGY CURABLE COMPOSITIONS COMPRISING POLYOLS

CROSS REFERENCE TO RELATED APPLICATIONS

The present application is a § 371 National Phase application based on PCT/GB2019/051858 filed Jul. 1, 2019, which claims the benefit of U.S. Provisional Application Nos. 62/697,438 filed Jul. 13, 2018, 62/716,472 filed Aug. 9, 2018, 62/729,097 filed Sep. 10, 2018, 62/760,142 filed Nov. 13, 2018 and 62/818,772, filed Mar. 15, 2019 the subject matter of each of which is incorporated by reference in their entirety.

The present invention relates to the use of alcohols and especially polyols to promote the energy-curing of compositions comprising ethylenically unsaturated monomers and oligomers.

WO2011/021052 describes UV-curable inkjet compositions comprising greater than 30% (w/w) of solvent. The solvent is removed evaporatively before the inks are UV-cured. The capacity for any hydroxyl-functional material, and especially polyols to enhance the cure under UV or EB is neither described not alluded to.

WO2013/093414 similarly describes solvent-containing UV-curable inkjet compositions, with the intention of printing food packaging. Again, the solvent is evaporatively removed prior to UV-curing, and a further requisite to enable this evaporative drying is that the solvents have boiling points of less than 170° C. Again, the capacity of polyols to promote the cure of such compositions is not revealed.

WO2017/151137 describes EB-curable inkjet compositions comprising monofunctional monomers bearing a hydroxy group, such as hydroxybutyl acrylate. The capacity of polyol compounds to promote EB-cure is not revealed.

WO2017/180496 and WO2017/180491 describe EB-curable compositions which can optionally comprise ethylenically unsaturated monomers/oligomers comprising poly(alkylene oxide) sub-units. Similarly, WO2015/148094, describes the use of ethylenically unsaturated monomers/oligomers comprising poly(alkylene oxide) sub-units, which promoted the cure of UV-curable compositions. However, none of these records describe the use of polyol containing (poly(alkylene oxide)) substances, which are essentially free of any ethylenically-unsaturated groups, in energy-curable compositions. U.S. Pat. No. 6,846,851 describes the use of poly(ethylene glycol) diacrylates in water-based UV-curable compositions, where they acted as reactive humectants. Again, no mention was made of the use of essentially ethylenically unsaturated free analogous substances for EB-curing.

A number of patents describe UV-curable low migration inkjet compositions. U.S. Pat. No. 9,714,355 describes compositions comprising blends of low migration photoinitiators, including type I (cleavage) photoinitiators. U.S. Pat. No. 9,550,898 similarly describes UV-curable low migration inkjet compositions which also contain acylphosphine oxide photoinitiators as the type I photoinitiator. U.S. Pat. No. 9,796,865 describes UV-curable low migration inkjet compositions comprising hybrid monomers such as 2-(2-Vinyloxyethoxy)ethyl acrylate ('VEEA'). U.S. Pat. No. 9,701,856 describes how inkjet compositions comprising essentially VEEA as the only monomer can be combined with thiols to deliver low migration printable solutions.

From the identified prior art, the use of polyol substances to promote the cure of free-radically polymerizable compositions under the action of UV or electron beam radiation has not been revealed. The capacity of such substances to significantly reduce the amount of uncured ethylenically unsaturated monomers and oligomers in UV and electron beam cured coatings and inks is clearly beneficial, especially in sensitive applications where high conversion of monomers and oligomers is advantageous, such as the printing and coating of food packaging, pharmaceutical packaging, and the like. Increasing the conversion of ethylenically unsaturated monomers and oligomers during UV and EB-curing will consequently minimise the amount of unbound monomer that could diffuse from the printed ink or coating and cause contamination issues.

Thus, a particular objective of the present invention is to reduce the amount of contamination from cured inks/coatings in packaging applications. The present invention addresses this problem via the reduction or elimination of migratory compounds which are present in conventional inks/coatings and which cause undesirable contamination. Surprisingly, the present inventors have found that non-acrylated substances provide a solution to this problem.

No references describing the benefits of the inclusion of polyols, such as triethylene glycol in UV or EB-curable free-radically curable compositions have been identified. As such, it is believed that the current invention is the first recognized use of such substances to enhance the radiation cure of inks and coatings.

The use of polyols to promote the cure of UV-cationically polymerizable compositions is well known, such as the polymerisation of epoxides and/or vinyl ethers. However, their use in the promotion of UV-curable and EB-curable (free radically polymerizable) compositions comprising ethylenically unsaturated materials and specifically acrylated monomers and oligomers has not been previously described. The inventors have found that the inclusion of hydroxy-functional compounds, and preferably those compounds bearing greater than an average of one hydroxy group, are especially effective in promoting the UV-cure of inkjet compositions comprising any blend of ethylenically unsaturated monomers and oligomers. It will be appreciated that the term "any blend of ethylenically unsaturated monomers and oligomers" means that the composition can comprise one or more of such monomers and/or one or more of such oligomers, and preferably comprises at least one ethylenically unsaturated monomer and at least one ethylenically unsaturated oligomer. This finding has especially advantageous use in those applications requiring low migration of uncured monomers and oligomers after energy-curing; including the printing/coating of food packaging, pharmaceutical packaging, toys, household goods, display boards used to promote foodstuffs, and the like.

DETAILED DESCRIPTION OF THE INVENTION

According to the present invention, there is provided a radiation-curable ink or coating composition where the equivalent hydroxy value contributed by substances comprising any blend of primary and secondary alcohols is 2.5 mgKOH/g, or greater; wherein the substances comprising the alcohol groups satisfy the following general expression:

$$R^1-(CHR^2OH)_n$$

and wherein $R^1$ may be any organic residue, and $R^2$ may be a hydrogen or any organic residue. n can be any number equal to or greater than one, preferably equal to or greater than two. The radiation-curable ink or coating composition is suitably described as a low migration composition.

The invention covers the most surprising finding that the inclusion of alcohols, and especially polyols (substances comprising 2 or more hydroxyl groups), can promote the energy-curing (specifically UV, but also electron beam curing) of compositions comprising ethylenically unsaturated monomers and oligomers. The inclusion of such compounds into compositions suitable for inkjet printing which further comprise blends of acrylate monomers has been shown to provide a considerable reduction in the amount of uncured monomer present in an EB-cured ink film. This is an important finding for applications where high conversion of monomers and oligomers (especially of inkjet compositions) during UV or EB cure is beneficial; such as the printing of food packaging, pharmaceutical packaging, personal care packaging, etc. As well as inkjet, this finding will have potential in other printing/coating applications where low migration of monomers and oligomers from energy-cured inks and coatings is required, such as flexographic, gravure and offset printing. The use of alcohols and especially polyols such as glycerol, trimethylolpropane, propylene glycol and poly(ethylene glycol)s which are generally recognised as safe and have specific migration limits into food in excess of 6 mg/Kg (in Europe) is advantageous, as significant concentrations of such polyols can be incorporated into a formulation without running the risk of any migration of these polyols from a cured ink or coating into a packaged foodstuff exceeding the migration limit. Thus, the use of such polyols in energy-curable inks and coatings of the invention is highly beneficial, not just because of their capacity to significantly reduce the amounts of uncured monomers (and oligomers) after cure, but also due to their benign nature which results in minimal risk from their own migration.

A further aspect of the invention is that the hydroxy groups of the substances of the invention should preferentially be either primary or secondary alcohols.

Yet a further aspect of the invention is that the hydroxy value of the composition comprising any polyol compound should be at least 2.5, and more preferably greater than 5.0 mgKOH/g.

The current invention also includes the use of polyol solvents such as propylene glycol and glycerol. As is apparent from the review of the prior art, where solvents have been incorporated into energy-curable inkjet compositions in the past they have been done so to reduce the viscosity of the composition and to enable potentially lower film weights after evaporative drying of the solvent. To achieve the full benefit of the incorporation of the alcohols according to the invention it is most desirable that they are not evaporatively removed prior to the energy-curing stage. Thus, those alcohols having relatively high boiling points are preferable, and a further aspect of the invention is that the boiling points of any alcohol used in the current invention should preferably be greater than 150° C., and more preferably greater than 170° C.

As mentioned previously, no records of the use of alcohols, and especially polyols to promote the energy-cure of free-radically polymerizable compositions have been identified in the prior art. The finding that such compounds can promote the energy-curing of inks and coatings is not only surprising but, in the case of the polyol compounds which are essentially free of any ethylenically unsaturated groups according to the present invention, is counter to the perceived wisdom that non-reactive substances like these can have such a profound effect.

The inventors do not wish to be bound to any particular theory but consider that alcohols, particularly primary and secondary alcohols, encompassed by the invention promote cure under irradiation by UV or electron beam by generating free radicals that can initiate the polymerisation of ethylenically-unsaturated monomers and oligomers. The most likely mechanism for this postulate is the generation of free radicals at the α-carbon to the alcohol by the scission of a proton to produce the required free radical which initiates the free radical polymerisation of ethylenically unsaturated substances (especially acrylates).

The present application describes a number of examples suitable for inkjet printing, but it should be understood that the invention covers compositions that may be applied by any other coating/printing process where the effect of the inclusion of the alcohol containing substances, and especially of polyols having boiling points greater than 170° C., would be beneficial. Thus, flexographic, offset and gravure printing processes are covered by the current invention, as are roller, spray, and other coating methods.

What is most surprising is that the polyol compounds used in formulations and processes according to the current invention are so effective in reducing the amount of uncured monomer in UV-cured inks. Especially surprising is that those polyols which are essentially free of ethylenically unsaturated groups, for example poly(ethylene glycol), glycerol and trimethylolpropane, are so effective in reducing the amount of uncured monomer. This is a most unexpected finding and would not likely be anticipated by those skilled in the art. Indeed, it is the norm in the industry and understood by those skilled in the art that such compounds should be acrylated, for example by esterification with acrylic acid or transesterification with an acrylic acid ester, to enable them to participate in the energy-cured free radical polymerisation process. Thus, the inventors' finding that polyhydroxy-functional compounds can promote the UV- and EB-curing of compositions comprising ethylenically unsaturated substances is especially surprising. The use of such inventive substances in compositions and processes according to the current invention is significantly more effective in reducing the amount of uncured monomer (and oligomer) after UV-cure with a suitable photoinitiator package, compared with the use of a mono-alcohol containing substance further bearing a single acrylate group, such as hydroxybutyl acrylate as revealed in WO2017/151137. Indeed, the inventors have shown by way of their comparative examples that the inclusion of hydroxybutyl acrylate into a UV-curable inkjet composition had no observable significant impact on any lowering of the amount of uncured monomer detected in a cured ink film compared with compositions comprising substances according to the current invention.

The use of energy cure-promoting compounds according to the current invention is especially useful for low migration printing and coating applications, and more especially of food packaging where the lowest possible levels of uncured monomers in printed or coated articles would be desirable. In respect of any possible contamination of packaged foodstuffs arising from the print or coating, the use of compounds such as propylene glycol, glycerol and triethylene glycol is advantageous since they are generally recognised as being safe. Indeed, compounds such as glycerol are often used as humectants in foods intended for human consumption. In the EU, glycerol, TMP and polyethylene glycol have migration limits of 60 mg/Kg (60 mg per Kg of foodstuff).

As is apparent from the foregoing, the identified prior art has not disclosed, or alluded to, the use of polyol substances of the current invention, to promote the cure of compositions comprising ethylenically unsaturated monomers and oligomers under the action of UV and EB radiation.

The present invention is drawn to energy curable compositions comprising polyols and any blend of ethylenically unsaturated monomers and oligomers, i.e. compositions including ethylenically unsaturated monomers and/or ethylenically unsaturated oligomers. The polyols of the invention are essentially free of any ethylenically unsaturated groups. It is preferred that the polyol substances according to the invention have greater than one hydroxy group and preferably have boiling points in excess of 170° C.

Definitions

Energy Curing. Refers to either UV or EB-curing, although covers the use of any other actinic radiation.

UV Curing. UV curing, in the context of the current invention, is a process that uses UV light to initiate the free radical polymerization of ethylenically unsaturated monomers and oligomers. This can be achieved with any selection of UVA, UVB and UVC light and may be achieved via the optional incorporation of photoinitiators. It should be understood that the invention although directed towards the curing under UV light also encompasses visible light. Non-limiting UV sources such as the following can be used; low pressure mercury bulbs, medium pressure mercury bulbs, a xenon bulb, excimer lamps, a carbon arc lamp, a metal halide bulb, a UV-LED lamp or sunlight. It should be appreciated by those skilled in the art that any UV light source may be used to cure compositions prepared according to the current invention.

EB Curing. Compositions prepared according to the present invention are suitable for curing under the action of electron beam (EB) radiation. EB curing describes the use of electron beam radiation to polymerize a combination of monomers and oligomers onto a substrate. In the case of the invention the monomers and oligomers used are those which polymerise free radically, and hence contain ethylenically unsaturated groups, such as acrylate.

Low Migration: The compositions of the current invention lend themselves to applications including the printing of food packaging, pharmaceutical packaging, personal care and household packaging, display boards in supermarkets, etc. In all these applications it is advantageous that the cured ink, or coating, contains minimal amounts of uncured material that could leach ('migrate') out of the ink into the surrounding environment thereby causing unwanted contamination. This is of particular concern for food packaging where any contamination of the packaged food from undesirable, migratable, ink components should be minimized.

Hydroxy Value. This is a term well understood by those skilled in the art. It is a measure of the content of hydroxyl groups in a substance expressed in terms of the mass of potassium hydroxide (KOH) in milligrams equivalent to the hydroxyl content in one gram of the substance. As will be described later, compositions prepared according to the current invention preferably comprise those polyol substances comprising primary or secondary alcohols and the preferred hydroxy value of any ink or other composition prepared according to the invention should be greater than 2.5 mgKOH/g.

Molecular Weight. Unless otherwise stated, a reference to "molecular weight" or "average molecular weight" is preferably to the number average molecular weight ($M_n$). The molecular weight can be measured by those techniques known in the art such as gel permeation chromatography. For instance, molecular weight determination may be conducted on a Hewlett-Packard 1050 Series HPLC system equipped with two GPC Ultrastyragel columns, 103 and 104 Å (5 μm mixed, 300 mm×19 mm, Waters Millipore Corporation, Milford, Mass., USA) and THF as mobile phase. Preferably, molecular weight is calculated by comparison with a polystyrene standard. The skilled person will appreciate that this definition of molecular weight applies to polymeric materials which typically have a molecular weight distribution. The molecular weight of non-polymeric compounds, such as the simple molecules of glycerol and trimethylolpropane, are defined and calculated on the basis of the molecular structure of the compound.

The term "essentially free of any ethylenically unsaturated groups", as used herein to describe the alcohols of utility in the present invention, particularly refers to ethylenically unsaturated groups which are, or comprise, acrylate groups. As noted hereinabove, it is surprising that such non-acrylated substances have such utility. It will be appreciated that such non-acrylated alcohols may optionally comprise other unsaturated groups, for instance aromatic hydrocarbons, as described elsewhere herein.

The invention describes the most surprising finding that polyol compounds such as glycerol and trimethylolpropane can promote the cure of compositions comprising monomers and oligomers bearing ethylenically unsaturated groups, such as acrylates, under the action of UV (and EB) radiation. This surprising finding realizes its effect by delivering lower amounts of uncured monomer after curing compared with compositions that do not contain such compounds. The finding has particular relevance for applications such as the printing of food packaging, which require that any ink or coating after application has low levels of substances that might migrate from the ink and/or coating and thence contaminate the surrounding environment, in case of food packaging the foodstuff itself. With the increasing awareness of the potential for contamination risks associated with food packaging, then any printing/coating process that can deliver an acceptably low migration risk has considerable worth. The current invention, via the use of compositions comprising polyols, provides a solution in this respect.

One of the surprising findings of the invention is that alcohols and especially polyols which promote the UV-cure of the compositions can do so without having any polymerizable (ethylenically unsaturated) groups incorporated into their structure. This most surprising finding has not been disclosed, or alluded to, in the prior art and is one which runs counter to currently perceived wisdom. The inventors do not wish to be bound by any theory as to why this should be the case but conjecture that polyols, such as glycerol and poly(ethylene glycol), are able to act as co-initiators of free radical polymerization. They may achieve this via a transfer process at the carbon adjacent to the hydroxy group. For primary and secondary alcohols it is likely that this is a H-transfer process. Thus, polyols may act synergistically with photoinitiators to produce free radicals that may initiate the polymerization of ethylenically unsaturated monomers and oligomers. It can be readily envisaged that substances comprising more than one primary and/or secondary alcohol as part of their structure would have the capacity to form a plurality of free radicals via this postulated free radical transfer process. This would lead to the potential formation of a more highly crosslinked network during the energy-curing process, which conventional wisdom indicates would lead to a lowering of the amount of uncured monomers and oligomers in any cured coating/ink composition.

A further aspect of the invention is that the hydroxy value of the inventive compositions contributed by primary and secondary alcohols should preferably be ≥2.5, and more preferably ≥5.0 mgKOH/g equivalent. The inventors have calculated the theoretical hydroxy values of a number of the inventive examples to substantiate this.

The present invention encompasses any substance comprising one or more hydroxyl groups according to the following, non-limiting, general expression may be used:

where $R^1$ may be any organic residue, and where $R^2$ may be a hydrogen or any organic residue. In this instance an organic residue refers to any possible sub-unit that may be bound to the polyol of the invention and includes, but is not limited to; alkanes, aromatic hydrocarbons, heterocyclics, polyesters, polyamides, polyacrylics, styrene-acrylic copolymers, polyurethanes, polyethers. In the case of polyethers, the invention encompasses polyols which have been reacted with ethylene oxide, propylene oxide and higher alkylene oxides. Polyethers encompassed by the invention also include poly(ethylene glycol)s, poly(propylene glycol)s and higher poly(alkylene oxide)s. The degree of hydroxyl content of the substance should be two, or greater. n can be any number equal to or greater than one, preferably equal to or greater than two.

It is further preferred that the polyol used in the present invention should have a boiling point of greater than 150° C., preferably greater than 170° C., and most preferably greater than 180° C. at atmospheric pressure (760 mmHg). A further aspect of the invention is that the molecular weight of the polyol used is preferably <5,000, more preferably <2,500 and in the instance of inkjet compositions especially preferably <1,500.

There is no restriction on the amount of any blend of polyol compounds according to the invention that can be incorporated into a free radically polymerizable energy-curable composition other than that it is sufficient satisfy the minimum hydroxy value criterion of the composition, namely that the contribution to the hydroxy value of the compositions provided by primary and secondary alcohols of the polyols of the invention is ≥2.5 mgKOH/g.

Preferably, the total amount of said blend of primary and secondary alcohols is less than 25.0% (w/w) of the composition, preferably less than 20.0% (w/w) and more preferably less than 10.0% (w/w) of the composition. The total amount of said blend of primary and secondary alcohols is preferably at least 1.0% (w/w), preferably at least 2.0% (w/w), preferably at least 3.0% (w/w), preferably at least 4.0% (w/w), and preferably about 5.0% (w/w) of the composition. The total amount of said blend of primary and secondary alcohols is preferably from 4.0% (w/w) to about 10.0% (w/w). Advantageously, the total amount of said blend of primary and secondary alcohols is no more than 7.5% (w/w) or no more than 5.0% (w/w) of the composition.

In yet a further aspect of the invention, compositions of the current invention may optionally comprise any blend of photoinitiators. Such compositions may then be cured by UV or a combined UV and EB curing process, as revealed by WO2017/180491 and WO2017/180496. Where the inks or coatings of the invention are intended for the application to food packaging then those photoinitiators having low migration potential should be used. Suitable photoinitiators will be described subsequently.

Preferably, the total concentration of photoinitiators is less than 5.0 wt. %.

Compositions of the invention may comprise any blend of ethylenically unsaturated monomers and oligomers. Where the compositions are intended for the printing or coating of food packaging it is preferred that the concentration of monofunctional monomers be less than 20%, preferably less than 10% and most preferably less than 5% by weight of the total composition.

There is no restriction on the type, blend or concentration of free radical photoinitiators used and can include any of, but not limited to the following (and combinations thereof):
α-hydroxyketones such as; 1-hydroxy-cyclohexyl-phenyl-ketone; 2-hydroxy-2-methyl-1-phenyl-1-propanone; 2-hydroxy-2-methyl-4'-tert-butyl-propiophenone; 2-hydroxy-4'-(2-hydroxyethoxy)-2-methyl-propiophenone; 2-hydroxy-4'-(2-hydroxypropoxy)-2-methyl-propiophenone; oligo 2-hydroxy-2-methyl-1-[4-(1-methyl-vinyl)phenyl]propanone; bis[4-(2-hydroxy-2-methylpropionyl)phenyl]methane; 2-Hydroxy-1-[1-[4-(2-hydroxy-2-methylpropanoyl)phenyl]-1,3,3-trimethylindan-5-yl]-2-methylpropan-1-one and 2-Hydroxy-1-[4-[4-(2-hydroxy-2-methylpropanoyl)phenoxy]phenyl]-2-methylpropan-1-one;
acylphosphine oxides such as; 2,4,6-trimethylbenzoyl-diphenylphosphine oxide; ethyl (2,4,6-trimethylbenzoyl) phenyl phosphinate, bis-(2,4,6-trimethylbenzoyl)-phenylphosphine oxide; and bis(2,6-dimethoxybenzoyl)-2,4,4-trimethylpentylphosphinoxide.
α-aminoketones such as; 2-methyl-1-[4-(methylthio)phenyl]-2-morpholinopropan-1-one; 2-benzyl-2-dimethylamino-1-(4-morpholinophenyl)-butan-1-one; and 2-dimethylamino-2-(4-methyl-benzyl)-1-(4-morpholin-4-yl-phenyl)-butan-1-one;
thioxanthones such as; 2-4-diethylthioxanthone, isopropylthioxanthone, 2-chlorothioxanthone, and 1-chloro-4-propoxythioxanthone;
benzophenones such as; such as benzophenone, 4-phenyl-benzophenone, and 4-methylbenzophenone; methyl-2-benzoylbenzoate; 4-benzoyl-4-methyldiphenyl sulphide; 4-hydroxybenzophenone; 2,4,6-trimethyl benzophenone, 4,4-bis(diethylamino)benzophenone; benzophenone-2-carboxy(tetraethoxy)acrylate; 4-hydroxybenzophenone laurate and 1-[-4-[benzoylphenylsulpho]phenyl]-2-methyl-2-(4-methylphenylsulphonyl)propan-1-one;
phenylglyoxylates such as; phenyl glyoxylic acid methyl ester; oxy-phenyl-acetic acid 2-[hydroxyl-ethoxy]-ethyl ester, or oxy-phenyl-acetic acid 2-[2-oxo-2-phenyl-acetoxy-ethoxy]-ethyl ester;
oxime esters such as; 1-phenyl-1,2-propanedione-2-(O-ethoxycarbonyl)oxime; [1-(4-phenylsulfanylbenzoyl) heptylideneamino]benzoate, or [1-[9-ethyl-6-(2-methyl-benzoyl)carbazol-3-yl]-ethylideneamino]acetate.

Examples of other suitable photoinitiators include diethoxy acetophenone; benzil; benzil dimethyl ketal; titanocen radical initiators such as titanium-bis(η 5-2,4-cyclopentadien-1-yl)-bis-[2,6-difluoro-3-(1H-pyrrol-1-yl) phenyl]; 9-fluorenone; camphorquinone; 2-ethyl anthraquinone; and the like.

An amine synergist may also be optionally included in the formulation. Suitable examples include, but are not limited to, the following: Aromatic amines such as; 2-(dimethylamino)ethylbenzoate; N-phenyl glycine; benzoic acid, 4-(dimethylamino)-, 1,1'-[(methylimino)di-2,1-ethanediyl] ester; and simple alkyl esters of 4-(N,N-dimethylamino)benzoic acid, with ethyl, amyl, 2-butoxyethyl and 2-ethylhexyl esters being particularly preferred; other positional isomers of N,N-dimethylamino)benzoic acid esters are also suitable;

Aliphatic amines such as N-methyldiethanolamine, triethanolamine and tri-isopropanolamine;

Also aminoacrylates and amine modified polyether acrylates, including but not limited to; EBECRYL 80, EBECRYL 81, EBECRYL 83, EBECRYL 85, EBECRYL 880, EBECRYL LEO 10551, EBECRYL LEO 10552, EBECRYL LEO 10553, EBECRYL 7100, EBECRYL P115 and EBECRYL P116 available from ALLNEX; CN501, CN550, CN UVA421, CN3705, CN3715, CN3755, CN381 and CN386, all available from Sartomer; GENOMER 5142, GENOMER 5161, GENOMER 5271 and GENOMER 5275 from RAHN; PHOTOMER 4771, PHOTOMER 4967, PHOTOMER 5006, PHOTOMER 4775, PHOTOMER 5662, PHOTOMER 5850, PHOTOMER 5930, and PHOTOMER 4250 all available from IGM, LAROMER LR8996, LAROMER LR8869, LAROMER LR8889, LAROMER LR8997, LAROMER PO 83F, LAROMER PO 84F, LAROMER PO 94F, LAROMER PO 9067, LAROMER PO 9103, LAROMER PO 9106 and LAROMER P077F, all available from BASF; AGISYN 701, AGISYN 702, AGISYN 703, NeoRad P-81 and NeoRad P-85 ex DSM-AGI.

Polymeric photoinitiators and sensitizers are also suitable, including, for example, polymeric aminobenzoates (GENOPOL AB-1 or AB-2 from RAHN, Omnipol ASA from IGM or Speedcure 7040 from Lambson), polymeric benzophenone derivatives (GENOPOL BP-1 or BP-2 from RAHN, Omnipol BP, Omnipol BP2702 or Omnipol 682 from IGM or Speedcure 7005 from Lambson), polymeric thioxanthone derivatives (GENOPOL TX-1 or TX-2 from RAHN, Omnipol TX from IGM or Speedcure 7010 from Lambson), polymeric aminoalkylphenones such as Omnipol 910 from IGM; polymeric benzoyl formate esters such as Omnipol 2712 from IGM; and the polymeric sensitizer Omnipol SZ from IGM.

Since the compositions of the current invention are intended for use in low migration applications printing and coating applications it is preferred that photoinitiators having low migration potential are used. Therefore, polymeric, polymerizable and multifunctional types are preferred.

Compositions according to the invention may comprise any amount of any blend of free radically polymerizable monomers and oligomers.

Examples of suitable monofunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts: isobutyl acrylate; cyclohexyl acrylate; iso-octyl acrylate; n-octyl acrylate; isodecyl acrylate; iso-nonyl acrylate; octyl/decyl acrylate; lauryl acrylate; 2-propyl heptyl acrylate; tridecyl acrylate; hexadecyl acylate; stearyl acrylate; iso-stearyl acrylate; behenyl acrylate; tetrahydrofurfuryl acrylate; 4-t.butyl cyclohexyl acrylate; 3,3,5-trimethylcyclohexane acrylate; isobornyl acrylate; dicyclopentyl acrylate; dihydrodicyclopentadienyl acrylate; dicyclopentenyloxyethyl acrylate; dicyclopentanyl acrylate; benzyl acrylate; phenoxyethyl acrylate; 2-hydroxy-3-phenoxypropyl acrylate; alkoxylated nonylphenol acrylate; cumyl phenoxyethyl acrylate; cyclic trimethylolpropane formal acrylate; 2(2-ethoxyethoxy) ethyl acrylate; polyethylene glycol monoacrylate; polypropylene glycol monoacrylate; caprolactone acrylate; ethoxylated methoxy polyethylene glycol acrylate; methoxy triethylene glycol acrylate; tripropyleneglycol monomethyl ether acrylate; diethylenglycol butyl ether acrylate; alkoxylated tetrahydrofurfuryl acrylate; ethoxylated ethyl hexyl acrylate; alkoxylated phenol acrylate; ethoxylated phenol acrylate; ethoxylated nonyl phenol acrylate; propoxylated nonyl phenol acylate; polyethylene glycol o-phenyl phenyl ether acrylate; ethoxylated p-cumyl phenol acrylate; ethoxylated nonyl phenol acrylate; alkoxylated lauryl acrylate; ethoxylated tristyrylphenol acrylate; N-(acryloyloxyethyl)hexahydrophthalimide; N-butyl 1,2 (acryloyloxy) ethyl carbamate; acryloyl oxyethyl hydrogen succinate; octoxypolyethylene glycol acrylate; octafluoropentyl acrylate; 2-isocyanato ethyl acrylate; acetoacetoxy ethyl acrylate; 2-methoxyethyl acrylate; dimethyl aminoethyl acrylate; 2-carboxyethyl acrylate; 4-hydroxy butyl acrylate.

Since compositions prepared according to the current invention are preferably intended for low migration printing and coating applications, including the printing and coating of food packaging then the amount of any monofunctional monomer used should be limited so as to reduce the risk associated with the migration of uncured monomer present in a UV-cured ink or coating. Therefore, another aspect of the invention is that the amount of any individual monofunctional monomer should be 20% (w/w) or less, preferably 10% (w/w) or less, and most preferably 5% (w/w) less of the total composition.

Where monomers are used in the preparation of inventive compositions it is preferable that they be multifunctional with respect to their polymerizable groups. Multifunctional monomers, having 2 or more ethylenically unsaturated groups, such as acrylate, have a greater probability of reacting into the UV-cured ink or coating compared with a monofunctional monomer, thereby reducing the risk of potential contamination arising from uncured monomer. Examples of suitable multifunctional ethylenically unsaturated monomers include but are not limited to the following (and combinations thereof), where the terms ethoxylated refers to chain extended compounds through the use of ethyleneoxide, propoxylated refers to chain extended compounds through the use of propylene oxide, and alkoxylated refers to chain extended compounds using either or both ethyleneoxide and propylene oxide. Equivalent methacrylate compounds are also capable of being used, although those skilled in the art will appreciate that methacrylate compounds have lower reactivity than their equivalent acrylate counterparts: 1,3-butylene glycol diacrylate; 1,4-butanediol diacrylate; neopentyl glycol diacrylate; ethoxylated neopentyl glycol diacrylate; propoxylated neopentyl glycol diacrylate; 2-methyl-1,3-propanediyl ethoxy acrylate; 2-methyl-1,3-propanediol diacrylate; ethoxylated 2-methyl-1,3-propanediol diacrylate; 3 methyl 1,5-pentanediol diacrylate; 2-butyl-2-ethyl-1,3-propanediol diacrylate; 1,6-hexanediol diacrylate; alkoxylated hexanediol diacrylate; ethoxylated hexanediol diacrylate; propoxylated hexanediol diacrylate; 1,9-nonanediol diacrylate; 1,10 decanediol diacrylate; ethoxylated hexanediol diacrylate; alkoxylated hexanediol diacrylate; diethyleneglycol diacrylate; triethylene glycol diacrylate; tetraethylene glycol diacrylate; polyethylene glycol diacrylate; propoxylated ethylene glycol diacrylate; dipropylene glycol diacrylate; tripropyleneglycol diacrylate; polypropylene glycol diacrylate; poly (tetramethylene glycol) diacrylate; cyclohexane dimethanol diacrylate; ethoxylated cyclohexane dimethanol diacrylate; alkoxylated cyclohexane dimethanol diacrylate; polybutadiene diacrylate; hydroxypivalyl hydroxypivalate diacrylate; tricyclodecanedimethanol diacrylate; 1,4-butanediylbis[oxy(2-hydroxy-3,1-propanediyl)]diacrylate; ethoxylated bisphenol A diacrylate; propoxylated bisphenol A diacrylate; propoxylated ethoxylated bisphenol A diacrylate; ethoxylated bisphenol F diacrylate; 2-(2-Vinyloxyethoxy)ethyl acrylate; dioxane glycol diacrylate; ethoxylated glycerol triacrylate; glycerol propoxylate triacrylate; pentaerythritol triacrylate; trimethylolpropane triacrylate; caprolactone modified trimethylol propane triacrylate; ethoxylated trimethylolpropane triacrylate; propoxylated trimethylol propane triacrylate; tris (2-hydroxy ethyl) isocyanurate triacrylate; e-caprolactone modified tris (2-hydroxy ethyl) isocyanurate triacrylate; melamine acrylate oligomer; pentaerythritol tetraacrylate; ethoxylated pentaerythritol tetraacrylate; di-trimethylolpropane tetra acrylate; dipentaerythritol pentaaacrylate; dipentaerythritol hexaacrylate; ethoxylated dipentaerythritol hexaacrylate.

Examples of monomers comprising free-radically polymerizable groups other than acrylate include N-vinyl amides. Examples of N-vinyl amides include but are not limited to N-vinylcaprolactam (NVC), N-vinyl pyrollidone (NVP), diacetone acrylamide, N-vinyl carbazole, N-acryloxyoxy ethylcyclohexanedicarboximide, N-vinyl imidazole, N-vinyl-N-methylacetamide (VIMA) or acryloyl morpholine (ACMO). Vinyl ethers such as 2-(2-vinyloxyethoxy)ethyl (meth)acrylate (VEEA, VEEM), diethylene glycol divinyl ether (DVE2), triethylene glycol divinyl ether (DVE3), ethyl vinyl ether, n-butyl vinyl ether, iso-butyl vinyl ether, tert-butyl vinyl ether, cyclohexyl vinyl ether (CHVE), 2-ethyl-hexyl vinyl ether (EHVE), dodecyl vinyl ether (DDVE), octadecyl vinyl ether (ODVE), 1-2-butanediol divinyl ether (BDDVE), 1-4, cyclohexanedimethanol divinylether (CHDM-di), hydroxybutyl vinylether (HBVE), 1-4-cyclohexanedimethanolmono vinylether (CHDM-mono), 1,2,4-trivinylcyclohexane (TVCH), vinylphosphonic acid dimethylester (VPA) or vinylphosphonic acid dimethyl ester (VPADME).

As well as, or in place of, free radically-polymerizable monomers any concentration and type of free-radically polymerizable oligomer, including but not restricted to polyurethane acrylates, polyester acrylates, polyether acrylates and epoxy acrylates may be used. Epoxy acrylates are an especially preferred class of material as these are substances encompassed by the invention.

Where the compositions of the invention require colourants, suitable colorants include, but are not limited to organic or inorganic pigments and dyes. The dyes include but are not limited to azo dyes, anthraquinone dyes, xanthene dyes, azine dyes, combinations thereof and the like. Organic pigments may be one pigment or a combination of pigments, such as for instance Pigment Yellow Numbers 12, 13, 14, 17, 74, 83, 114, 126, 127, 150, 155, 174, 180, 188; Pigment Red Numbers 2, 22, 23, 48:1, 48:2, 52, 52:1, 53, 57:1, 112, 122, 166, 170, 184, 202, 266, 269; Pigment Orange Numbers 5, 16, 34, 36, 71; Pigment Blue Numbers 15, 15:3, 15:4; Pigment Violet Numbers 3, 19, 23, 27; and/or Pigment Green Number 7. Inorganic pigments may be one of the following non-limiting pigments: iron oxides, titanium dioxides, chromium oxides, ferric ammonium ferrocyanides, ferric oxide blacks, Pigment Black Number 7 and/or Pigment White Numbers 6 and 7. Other organic and inorganic pigments and dyes can also be employed, as well as combinations that achieve the colors desired.

The energy-curable compositions of the invention may also contain other components which enable them to perform in their intended application. These other ink components include, but are not restricted to; stabilizers, wetting aids, slip agents, inert resins, antifoams, fillers, rheological aids, amine synergists, etc.

The compositions of the invention may also optionally comprise any blend of acrylic polymer or copolymer which is dissolved into it. These polymers are usually prepared by the (thermal) free radical polymerization of blends of monomers including, but not restricted to, styrene, butyl (meth) acrylate, ethyl (meth)acrylate, methyl (meth)acrylate, isobutyl (meth)acrylate. The acrylic polymer preferably has an average molecular weight of less than 20,000 g/mole and more preferably less than 10,000 g/mole. The molecular weight of such polymers can be measured by those techniques known in the art such as gel permeation chromatography. Examples of acrylic polymers include those supplied from Dianal, Elvacite Rohm and Haas and DSM, amongst others. The acrylic polymer is preferably present in the compositions at a concentration of between 2 and 20% (w/w).

Compositions of the current invention are preferably essentially free of any aprotic solvent, and protic solvents with boiling points of less than 150° C. However, if required, compositions of the current invention can be diluted with such solvents. Both organic and aqueous solvents may be used to dilute the curable compositions of the invention. The preferred maximum amount of any solvent that could be included in an ink composition is 10% (w/w).

Low migration compositions according to the current invention preferably use photoinitiators having low migration potential. Any combination and concentration of low migration potential photoinitiators may be used and types include, but are not restricted to; polymeric, polymerizable, difunctional, multifunctional photoinitiators. Both type I and type II photoinitiators within those classes are suitable. Suitable polymeric photoinitiators have previously been described. Other photoinitiators suitable for low migration applications include, 1-[4-(2-Hydroxyethoxy)-phenyl]-2-hydroxy-2-methyl-1-propane-1-one, Oligo-[2-Hydroxy-2-methyl-1-((4-(1-methylvinyl)phenyl) propanone], Poly (oxy-1,2 ethanedyil)-alpha-(4-(dimethylamino)benzoyl)-omega-((4-(dimethylamino)benzoyl)oxy)-(9C1), 2-Hydroxy-1-{4-[4-(2-hydroxy-2-methyl-propionyl)-benzyl]-phenyl}-2-methyl-propan-1-one, 2-hydroxy-1-[4-(4-(2-hydroxy-2-methylpropionyl)phenoxy)phenyl]-2-methyl propan-1-one. Photoinitiators which are suitable for low migration may include any of those listed in EUPIA's 'Suitability List of Photo-initiators for Low Migration UV Printing Inks and Varnishes', especially those in Group 1A and 1B. Any UV light source can be used including, but not limited to, UV-LED (including but not limited to those emitting UV light at 355, 365, 377, 385, 395 and 405 nm), high-pressure mercury bulb, a medium-pressure mercury bulb, a xenon bulb, a carbon arc lamp, a metal halide bulb, or sunlight. It should be appreciated by those skilled in the art that any UV light source may be used to cure compositions prepared according to the current invention.

A stabilizer may also be used in the composition to ensure good pot life of the ink, examples of which are nitroxy based stabilizers such as OHTEMPO, TEMPO, and Irgastab UV10. Phenolic stabilizers such as hydroquinone (HQ), methyletherhydroquinone (MEHQ), butylhydroxytoluene (BHT) and 2,6-di-tert-butyl-N,N-dimethylamino-p-cresol. Nitrosophenylhydroxylamine (NPHA) base inhibitors NPHA, amine salts, and metal salts (Al salt, N-PAL) plus the aromatic amine inhibitors diphenylamine (DPA) and phenylenediamine (PPD). Other suitable stabilizers are florstab UV-1, UV-8, Genorad 16 and 18.

Included in the ink formulation can be a suitable de-aerator, these prevent the formation of air inclusions and pinholes in the cured coating. These also reduce rectified diffusion which can cause reliability issues in the printhead. The following, non-limiting, products are available from EVONIK: TEGO AIREX 900, 910, 916, 920, 931, 936, 940, 944, 945, 950, 962, 980, 986.

Defoamers can also be included in the formulation, these prevent the formation of foam during manufacture of the ink and also while jetting. These are particularly important with recirculating printheads. Suitable, non-limiting, defoamers include TEGO FOAMEX N, FOAMEX 1488, 1495, 3062, 7447, 800, 8030, 805, 8050, 810, 815N, 822, 825, 830, 831, 835, 840, 842, 843, 845, 855, 860, 883, TEGO FOAMEX K3, TEGO FOAMEX K7/K8 and TEGO TWIN 4000 available from EVONIK. Available from BYK is BYK-066N, 088, 055, 057, 1790, 020, BYK-A 530, 067A, and BYK 354.

Surface Control Additives are often used to control the surface tension of the ink which is required to adjust the wetting on the face plate of the printhead and also to give the desired drop spread on the substrate or and in the case of multi pass inkjet printing wet on dry drop spread. They can also be used to control the level of slip and scratch resistance of the coating. Suitable surface control additives include but are not limited to TEGO FLOW300, 370, 425, TEGO GLIDE 100, 110, 130, 406, 410, 411, 415, 420, 432, 435, 440, 482, A115, B1484, TEGO GLIDE ZG 400, TEGO RAD2010, 2011, 2100, 2200N, 2250, 2300, 2500, 2600, 2650, 2700, TEGO TWIN 4000, 4100, TEGO WET 240, 250, 260, 265, 270, 280, 500, 505, 510 and TEGO WET KL245 all available from EVONIK. Available from BYK are BYK 333, 337, BYK UV3500, BYK 378, 347, 361, BYK UV3530, 3570, CERAFLOUR 998, 996, NANOBYK 3601, 3610, 3650 and CERMAT 258. From CYTEC EBECRYL 350, 1360, MODAFLOW 9200, EBECRYL 341. From SARTOMER the aliphatic silicone acrylate CN9800 may be used.

Where ink and coating compositions are applied to the (non-contact) surface of primary or secondary packaging intended for foodstuffs, then any contamination from the package impacting the foodstuff should fall within the guidelines set out by Article 3 of Regulation (EC) No 1935/2004 (supplemented by EC No 10/2011), as recommended by EUPIA, requiring that materials and articles in contact with food;

"shall be manufactured in accordance with good manufacturing practices, so that under normal or foreseeable conditions of use, they do not transfer their constituents to food in quantities which could:
  endanger human health; or
  bring about an unacceptable change in the composition of the food; or
  bring about a deterioration in the organoleptic characteristics thereof"

EUPIA has recommended that Article 3 of this provision be followed when producing printed matter for food packaging and has produced a detailed guideline for the selection of raw materials intended for printing inks for food packaging, along with guidelines on the testing of printed matter to ensure that regulatory requirements are achieved. Where no SML exists for a specific component then the following migration limits apply;

"A target migration limit of no concern for non-evaluated substances of 10 ppb is the ultimate objective, to be consistent with other food contact materials.

In particular, a substance is acceptable if its specific migration does not exceed:
  10 ppb, in case of insufficient toxicological data
  50 ppb if three negative mutagenicity tests requested by EFSA4 Guidelines are available
  above 50 ppb, if supported by favorable toxicological data and/or evaluation done in accordance with the EFSA Guidelines" (Extract from EuPIA Guideline on Printing Inks applied to the non-food contact surface of food packaging materials and articles, September 2009).

EUPIA also provides guidelines on how to measure the potential level of migratables arising from printed matter. For inks and coatings applied to the non-food contact surface of packaging (i.e. the outer surface), whether that be to the primary packaging or secondary packaging (labels and sleeves) then the most likely route for migratable species from the ink contaminating the foodstuff is by what is known as set-off migration. This is where printed matter is stacked or reeled prior to it being filled with food. Thus, the ink comes into contact with what will be the food-contact surface of the package and migratable components of the ink can diffuse into this surface. When the package is then filled with foodstuff, the contaminants from the ink which have diffused into the contact-surface of the package can then leach into the food causing a potential contamination issue.

Thus, any energy-curable fluid which is applied to either the primary or secondary packaging of foodstuff should not result in contamination of that foodstuff at levels exceeding the limits detailed above.

According to a further aspect of the present invention there is provided a process for preparing a printed substrate comprising printing the composition as defined hereinabove onto a substrate and curing. To effect curing, the composition may be exposed to both UV and EB radiation. For instance the composition may be partially cured using any SUBSTITUTE SHEET (RULE 26) combination of UV-LED lamps, prior to EB-curing. In a preferred embodiment, the composition is cured by EB radiation. It will be appreciated that the foregoing description of the other aspects of the invention, including the preferences thereof, is equally applicable to this aspect of the invention too.

According to a further aspect of the present invention there is provided a printed article comprising a composition as defined hereinabove and/or which is obtainable by the printing process as defined hereinabove. Thus, it will be appreciated that the printed article in particular comprises a cured coating derived from a curable composition as defined hereinabove. The substrate of the printed article is preferably a plastic film. The printed article is preferably a food packaging article. It will be appreciated that the foregoing description of the other aspects of the invention, including the preferences thereof, is equally applicable to this aspect of the invention too.

According to a further aspect of the invention, there is provided a method of reducing the amount of uncured monomer in a cured ink or coating composition comprising applying the composition as defined herein to a substrate and curing. It will be appreciated that said reduction of the amount of uncured monomer is relative to a cured ink or coating composition which does not comprise the blend of primary or secondary alcohols defined herein. It will be appreciated that the foregoing description of the other aspects of the invention, including the preferences thereof, is equally applicable to this aspect of the invention too.

According to a further aspect of the invention, there is provided the use of substances comprising any blend of primary or secondary alcohols as defined herein and in claim 1 to promote the energy-cure (preferably UV and/or electron beam cure) of free-radically polymerizable compositions. The foregoing description of all the other aspects of the invention, including the preferences thereof, is equally applicable to this aspect of the invention too.

The present invention has been described in detail, including the preferred embodiments thereof. However, it will be appreciated that those skilled in the art, upon consideration of the present disclosure, may make modifications and/or improvements on this invention that fall within the scope and spirit of the invention.

EXAMPLES

The following examples illustrate specific aspects of the present invention and are not intended to limit the scope thereof in any respect and should not be so construed.

Viscosity Measurements

The viscosities of the inks were measured using a Brookfield DV-II+ Pro Viscometer equipped with Spindle no. 18, at 100 rpm.

Curing the Inks for Extraction Testing

The inks were applied to 23 μm Melinex 813 (a polyester film) at 10 m, unless otherwise stated, and then cured 150 mJ/cm$^2$, using a Fusion UV Systems UV-Rig equipped with a medium pressure H-bulb. The belt speed was adjusted to deliver the required UV-dose of 150 mJ/cm$^2$, as measured by a calibrated International Light Technologies ILT 490 Profiling Belt Radiometer (covering the UV-A and UV-B ranges).

Assessing the Level of Extractable Monomer

The levels of unbound, unreacted monomer residues in a print were determined by a 'total extraction' test. This test involved soaking 30 cm$^2$ of the print in 2 ml of methanol, containing 0.005% (w/w) of MEHQ (stabilizer) for 24 hours at room temperature before the methanol solution was analyzed by GC-MS. The GC-MS was calibrated with known solutions of the monomers and the results are reported as the amount of uncured monomer per unit area of print, expressed as μg/dm$^2$.

Inks were prepared according to the compositions below and stirred until homogeneous using a Silverson mixer.

Ink Examples

Preliminary Investigation into the Impact of Polyols on the UV-Cure; UV-Curable Cyan Inkjet Compositions:

A series of compositions suitable for inkjet printing, comprising a blend of photoinitiators suitable for low migration printing, were prepared according to following formulation.

TABLE 1

UV-Curable Cyan Inkjet Compositions Comprising Polyols

| Component | % (w/w) Contribution |
|---|---|
| VEEA | 35.0 |
| 3-MePDDA | 35.0 |
| TMPEOTA | 3.5-11.5 |
| Acrylated Amine | 3.5 |
| Polyol | 0-8.0 |
| Irgacure 819 | 0.5 |
| Esacure KIP160 | 1.5 |
| Omnirad 127 | 2.0 |
| TegoGlide 410 | 2.0 |
| Cyan Dispersion | 9.0 |
| Total | 100.0 |

Notes:

VEEA = 2-(2-vinyloxyethoxy)ethyl acrylate

3-MePDDA = 3-Methylpentanediol diacrylate

TMPEOTA = Trimethylolpropane ethoxylate triacrylate (3 moles ethoxylation) (Sartomer SR454). The concentration of this monomer was adjusted to allow for the incorporation of the polyols.

Acrylated Amine = Sartomer CN3715

Irgacure 819 = Acylphosphine oxide photoinitiator, ex. IGM Resins

Esacure KIP160 = Difunctional hydroxyketone photoinitiator, ex. IGM Resins

Omnirad 127 = Difunctional hydroxyketone photoinitiator, ex. IGM Resins

Tego Glide 410 = silicone polyether surfactant, ex. Evonik

Cyan Dispersion = a proprietary dispersion containing 25.0% (w/w) of Pigment 15:4, the remainder comprising the dispersant, stabilizers and DPGDA Table 2 provides the details of the alcohol containing substance used in each example, along with the viscosity of the ink, the hydroxy value of the ink based on the theoretical content of primary and secondary alcohols, the amount of uncured monomer as determined by the previously described Extractable Analytical method and the extent of the reduction in the amount of uncured monomer expressed as a weight percentage reduction compared with the control (Comparative Example 1) composition.

TABLE 2

UV-Curable Cyan Inkjet Compositions Comprising Alcohol Containing Substances

| Example | Alcohol Substance | % (w/w) of Alcohol Substance | Viscosity @ 45° C. (mPa · s) | OHV (mgKOH/g) | Extractable VEEA (μg/dm$^2$) | % Reduction of Extractable VEEA | Extractable 3-MePDDA (μg/dm$^2$) | % Reduction of Extractable 3-MePDDA |
|---|---|---|---|---|---|---|---|---|
| Comparative 1 | — | — | 5.04 | 0 | 95.0 | — | 86.7 | — |
| Inventive 1 | DiPETA(EO)13 | 1.7 | 5.37 | 7.0 | 21.7 | 77 | 17.5 | 80 |
| Inventive 2 | DiPETA(EO)13 | 2.0 | 5.40 | 8.2 | 30.7 | 68 | 23.3 | 73 |
| Inventive 3 | DiPETA(EO)13 | 4.0 | 5.67 | 16.3 | 8.9 | 91 | 7.7 | 91 |
| Inventive 4 | DiPETA(EO)13 | 6.0 | 6.54 | 24.5 | 2.3 | 98 | 2.7 | 97 |
| Comparative 2 | HOBA | 1.7 | 5.07 | 7.0 | 80.0 | 16 | 86.7 | 0 |
| Comparative 3 | HOBA | 3.3 | 4.92 | 13.0 | 98.3 | 0 | 100.0 | 0 |
| Comparative 4 | HOBA | 6.6 | 4.80 | 25.9 | 71.7 | 25 | 81.7 | 6 |

Notes to Table 2:

DiPETA(EO)13 = Ethoxylated DiPentaerythritol with 13 moles ethoxylation.

HOBA = 4-Hydroxybutyl acrylate (a monofunctional acrylate monomer bearing one alcohol group as disclosed in WO2017151137)

OHV = Hydroxy Value of the ink expressed as mgKOH/g; as contributed by the polyol The results in Table 2 clearly show the effectiveness of the invention. What is particularly surprising is the profound effect that the incorporation of the ethoxylated dipentaerythritol has on the lowering of the amount of uncured monomer in the UV-cured ink films. This is achieved without this substance bearing any groups which would be anticipated as playing a part in the UV-curing process. Indeed, it would be anticipated through current understanding that, as a potentially non-reactive substance, it might have a detrimental impact on the UV (or EB) cure. This is evidently not the case. It is this finding along with those from the subsequent Inventive Examples that informed the inventors of the advantageous use of alcohol, and especially polyol compounds in energy-curing compositions to deliver lower levels of unreacted monomer and oligomer. This finding will have significant benefit in applications where low levels of uncured monomer and oligomer are highly desirable, such as the printing and coating of food packaging.

Significant lowering of the uncured monomer was achieved with hydroxy values as low as 7.0 mgKOH/g, particularly in the case of the ethoxylated dipentaerythritol. Comparative Examples 2, 3 and 4 which comprised 4-hydroxybutyl acrylate showed very little, if any, lowering of the amounts of uncured monomer in UV-cured ink films. This finding indicates that to have effect, the alcohol containing substance should ideally bear greater than 2 hydroxy groups.

To further illustrate this most surprising and unexpected finding, a further series of magenta inkjet compositions were prepared comprising different polyols. The general formulation used is provided in Table 3 and the results for the amounts of extracted monomer in Table 4.

TABLE 3

UV-Curable Magenta Inkjet Compositions Comprising Polyols

| Component | % (w/w) Contribution |
|---|---|
| VEEA | 20.0 |
| 3-MePDDA | 30.0 |
| DPGDA | 8.9-18.9 |
| DiTMPTA | 3.5 |
| Acrylated Amine 1 | 4.0 |
| Polyol | 0-10.0 |
| Irgacure 819 | 0.6 |
| Esacure KIP160 | 2.0 |
| Omnirad 127 | 2.0 |
| TegoGlide 410 | 2.0 |
| Magenta Dispersion | 17.0 |
| Total | 100.0 |

Notes to Table 3:
DPGDA = Dipropylene glycol diacrylate. The concentration of DPGDA was adjusted to allow for the incorporation of the polyols.
DiTMPTA = Ditrimethylolpropane tetraacrylate
Acrylated Amine 1 = CN3755, ex. Sartomer
Magenta Dispersion = a proprietary dispersion containing 21.0% (w/w) of Pigment Red 122, the remainder comprising the dispersant, stabilizers and DPGDA.

TABLE 4

Amounts of Uncured Monomer Extracted from the UV-Cured Magenta Inkjet Prints

| Example | Alcohol Substance[1] | % (w/w) of Alcohol Substance | Viscosity @ 45° C. (mPa·s) | OHV (mgKOH/g) | Extractable VEEA (μg/dm$^2$) | % Reduction of Extractable VEEA | Extractable 3-MePDDA (μg/dm$^2$) | % Reduction of Extractable 3-MePDDA |
|---|---|---|---|---|---|---|---|---|
| Comparative 5 | — | — | 9.15 | — | 198 | 31 | 314 | 40 |
| Inventive 5 | Glycerol | 7.5 | 10.1 | 137 | 56 | 80 | 90 | 83 |
| Inventive 6 | Propylene Glycol | 7.5 | 9.03 | 110 | 44 | 85 | 93 | 82 |
| Inventive 7 | Trimethylol Propane | 7.5 | 11.4 | 94 | 4.8 | 98 | 5.9 | 99 |
| Inventive 8 | TMP(EO)3[1] | 7.5 | 10.4 | 47 | 20 | 93 | 38 | 93 |
| Inventive 9 | TMP(EO)7[1] | 7.5 | 10.5 | 28 | 12.2 | 96 | 17.3 | 97 |
| Inventive 10 | TMP(EO)20[1] | 7.5 | 11.1 | 12 | 35 | 88 | 54 | 90 |
| Inventive 11 | Penta(EO)5[2] | 7.5 | 12.7 | 47 | 6.2 | 98 | 6.0 | 99 |
| Inventive 12 | Penta(EO)15[2] | 7.5 | 10.9 | 21 | 13.4 | 95 | 15.9 | 97 |
| Inventive 13 | Tripropylene Glycol | 7.5 | 9.24 | 43 | 42 | 85 | 100 | 81 |
| Inventive 14 | PEG200 | 7.5 | 9.63 | 42 | 28 | 90 | 66 | 87 |
| Inventive 15 | PEG600 | 2.5 | 9.48 | 4.7 | 60 | 79 | 78 | 85 |
| Inventive 16 | PEG600 | 5.0 | 10.2 | 9 | 28 | 90 | 47 | 91 |
| Inventive 17 | PEG600 | 7.5 | 10.4 | 14 | 21 | 93 | 34 | 93 |
| Inventive 18 | PEG600 | 10.0 | 10.8 | 18 | 9.2 | 97 | 11.3 | 98 |

Notes to Table 4:
[1]TMP(EO)x refers to ethoxylated trimethylolpropane, where x is the degree of ethoxylation.
[2]Penta(EO)x refers to ethoxylated pentaerythritol, where x is the degree of ethoxylation.

The results in Table 4 further demonstrate the impact of compositions comprising polyols bearing primary and secondary alcohols. What is clear, and most surprising, confirming the previous findings is that polyols bearing primary and/or secondary alcohols induce a significant lowering in the amount of uncured monomer after UV-curing. To the best of the inventors' knowledge this effect has not been previously reported. It is a highly useful finding for those printing and coating applications where the contamination from uncured monomers and oligomers must be minimized, notable the printing and coating of food packaging. As noted earlier the use of substances such as glycerol, propylene glycol and poly(ethylene glycol) in delivering this effect is in itself beneficial as a consequence of these materials' relatively benign nature.

To demonstrate how effective a highly functional polyol can be in reducing the amount of uncured monomer after both UV and EB-curing, two series of inks comprising the hexafunctional polyol DiPETA(EO)13 were prepared with ink hydroxy values ranging from zero to 20 mgKOH/g.

Table 5 shoes the formulations for the UV-curable ink set along with the amounts of uncured monomer for inks cured under the conditions previously described. Table 6 shows the formulations for the EB-curable ink set along with amounts of uncured monomer for 10 μm ink films on PET film cured with an EB dose of 35 kGy at an accelerating voltage of 100 keV as supplied by an AEB ADC lab EB-curing unit.

TABLE 5

UV-Curable Inks Comprising DiPETA(EO)13

|  | Comparative 6 | Inventive 19 | Inventive 20 | Inventive 21 | Inventive 22 |
| --- | --- | --- | --- | --- | --- |
| VEEA | 35.0 | 35.0 | 35.0 | 35.0 | 35.0 |
| 3-MePDDA | 35.0 | 35.0 | 35.0 | 35.0 | 35.0 |
| TMPEOTA | 11.0 | 10.4 | 9.8 | 8.5 | 6.1 |
| Acrylated Amine | 3.5 | 3.5 | 3.5 | 3.5 | 3.5 |
| DiPETA(EO)13 | — | 0.6 | 1.2 | 2.5 | 4.9 |
| Irgacure 819 | 0.5 | 0.5 | 0.5 | 0.5 | 0.5 |
| Esacure KIP160 | 2.0 | 2.0 | 2.0 | 2.0 | 2.0 |
| Irgacure 127 | 2.0 | 2.0 | 2.0 | 2.0 | 2.0 |
| TegoGlide 410 | 2.0 | 2.0 | 2.0 | 2.0 | 2.0 |
| Cyan Dispersion | 9.0 | 9.0 | 9.0 | 9.0 | 9.0 |
| Viscosity @ 45° C. (mPa · s) | 5.94 | 5.85 | 6.06 | 6.21 | 6.39 |
| Ink OH Value (kgKOH/g) | 0 | 2.5 | 5.0 | 10.0 | 20.0 |
| Extractable VEEA (μg/dm$^2$) | 113 | 49.2 | 10.8 | 7.7 | 1.6 |
| % Reduction of Extractable VEEA | — | 56 | 90 | 93 | 99 |
| Extractable 3-MePDDA (μg/dm$^2$) | 55 | 20.7 | 14.1 | 5.4 | 0.8 |
| % Reduction of Extractable 3-ePDDA | — | 62 | 74 | 90 | 99 |

The results in Table 5 clearly show the profound effect that the inclusion of even low concentrations of the hexafunctional polyol DiPETA(EO)13 can have in reducing the amount of uncured monomer after the UV-cure of a composition suitable for inkjet printing. Even at the lowest level of addition of 0.6% (being equivalent to an ink hydroxy value of 2.5 mgKOH/g), the amount of uncured monomer was reduced by greater than 50%. As noted previously, this most surprising finding has not been previously reported or alluded to in the prior art, to the best of the inventors' knowledge.

TABLE 6

EB-Curable Inks Comprising DiPETA(EO)13

|  | Comparative 7 | Inventive 23 | Inventive 24 | Inventive 25 | Inventive 26 |
| --- | --- | --- | --- | --- | --- |
| VEEA | 35.0 | 35.0 | 35.0 | 35.0 | 35.0 |
| 3-MePDDA | 35.0 | 35.0 | 35.0 | 35.0 | 35.0 |
| TMPEOTA | 9.0 | 8.4 | 7.8 | 6.5 | 4.1 |
| PEG400DA[1] | 10.0 | 10.0 | 10.0 | 10.0 | 10.0 |
| DiPETA(EO)13 | — | 0.6 | 1.2 | 2.5 | 4.9 |
| TegoGlide410 | 2.0 | 2.0 | 2.0 | 2.0 | 2.0 |
| Cyan Dispersion | 9.0 | 9.0 | 9.0 | 9.0 | 9.0 |
| Viscosity @ 45° C. (mPa · s) | 5.67 | 5.82 | 5.85 | 6.00 | 6.24 |
| Ink OH Value (kgKOH/g) | 0 | 2.5 | 5.0 | 10.0 | 20.0 |

TABLE 6-continued

EB-Curable Inks Comprising DiPETA(EO)13

|  | Comparative 7 | Inventive 23 | Inventive 24 | Inventive 25 | Inventive 26 |
|---|---|---|---|---|---|
| Extractable VEEA ($\mu g/dm^2$) | 21.0 | 9.5 | 8.3 | 2.7 | 1.4 |
| % Reduction of Extractable VEEA | — | 55 | 60 | 87 | 93 |
| Extractable 3-MePDDA ($\mu g/dm^2$) | 14.9 | 10.5 | 9.2 | 2.9 | 1.4 |
| % Reduction of Extractable 3-ePDDA | — | 30 | 38 | 81 | 91 |

Notes to Table 6
PEG400DA = Poly(ethylene glycol 400) Diacrylate

Again, the results in Table 6 show the impressive effect that the polyol DiPETA(EO)13 has on the lowering of the amount of uncured monomer after curing, in this case EB-curing. This shows that the use of polyols according to the invention are effective in both UV- and EB-curable compositions. The fact that polyols can induce such significant reductions in the amounts of uncured monomer after UV- or EB-curing makes their use especially suited to applications requiring the highest possible conversion of monomer such as the printing/coating of food packaging.

What is claimed is:

1. A low migration radiation curable ink or coating composition comprising any blend of primary and/or secondary alcohol, and any blend of free-radically polymerisable ethylenically unsaturated monomers, where the equivalent hydroxy value of the composition contributed by substances comprising any blend of primary and/or secondary alcohols is 2.5 mgKOH/g or greater;
wherein the alcohol is selected from any of propylene glycol, trimethylolpropane, glycerol, diethylene glycol, triethylene glycol, tetraethylene glycol, dipropylene glycol, tripropylene glycol, poly(ethylene glycol), poly(propylene glycol), ethoxylated trimethylolpropane, ethoxylated pentaerythritol, ethoxylated dipentaerythritol, and combinations thereof, and wherein the total amount of the blend of primary and/or secondary alcohols is no more than 7.5% (w/w) of the composition,
and wherein the ink composition is free of protic solvents with boiling points of less than 150° C.

2. The composition of claim 1 further comprising one or more photoinitiators.

3. The composition of claim 2, wherein the photoinitiators are suitable for low migration printing.

4. The composition of claim 1, wherein the alcohol is essentially free of any ethylenically unsaturated group.

5. The composition of claim 1, wherein the alcohol is a polyol having a molecular weight of less than 5,000, more preferably less than 2,500 and most preferably less than 1,500 g/mol.

6. The composition of claim 5, wherein the polyol has a boiling point of greater than 170° C.

7. The composition of claim 1 having an equivalent hydroxy value of 5.0 mgKOH/g, or greater.

8. The composition of claim 1, wherein the amount of detectable uncured monomer or oligomer is reduced by at least 25%, compared with an equivalent composition comprising none of the alcohol-bearing substance.

9. The composition of claim 1, further comprising one or more colorants.

10. The composition of claim 1, which is an inkjet ink, or a flexographic ink, or an offset ink.

11. The composition of claim 1, which is UV-curable.

12. The composition of claim 1, which is EB-curable.

13. A process for preparing a printed substrate, comprising printing the composition of claim 1 onto a substrate and curing.

14. The process of claim 13, wherein the composition is exposed to both UV and EB radiation.

15. The process of claim 13, wherein the composition is partially cured using any combination of UV-LED lamps, prior to EB-curing.

16. A printed article comprising a cured printed coating derived from the curable composition defined in claim 1.

17. The printed article of claim 16 comprising a substrate which is a plastic film.

18. A method of reducing the amount of migratable monomer in a cured ink or coating composition comprising the process of claim 13.

19. A low migration radiation curable ink or coating composition of claim 1 wherein the ink composition has a maximum amount of any solvent of 10% (w/w).

* * * * *